United States Patent
Kim et al.

(10) Patent No.: US 9,873,653 B2
(45) Date of Patent: *Jan. 23, 2018

(54) HETEROGENEOUS CATALYST FOR PRODUCTION OF 3-HYDROXYPROPIONIC ACID FROM ALLYL ALCOHOL, AND METHOD FOR PREPARATION OF 3-HYDROXYPROPIONIC ACID FROM ALLYL ALCOHOL USING THE SAME

(71) Applicants: LG CHEM, LTD., Seoul (KR); Industry-Academic Cooperation Foundation, Yonsei University, Seoul (KR)

(72) Inventors: Dae Sung Kim, Daejeon (KR); Won Jae Lee, Daejeon (KR); Yong-Jin Choe, Daejeon (KR); Hyunjoo Lee, Daejeon (KR); Sungpil Yang, Seoul (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/579,480

(22) Filed: Dec. 22, 2014

(65) Prior Publication Data

US 2016/0096170 A1 Apr. 7, 2016

(30) Foreign Application Priority Data

Oct. 7, 2014 (KR) .................. 10-2014-0134826

(51) Int. Cl.
| | | |
|---|---|---|
| *B01J 35/02* | (2006.01) | |
| *B01J 23/10* | (2006.01) | |
| *B01J 23/52* | (2006.01) | |
| *C07C 51/25* | (2006.01) | |
| *B01J 23/66* | (2006.01) | |
| *B01J 35/00* | (2006.01) | |
| *B01J 37/02* | (2006.01) | |

(52) U.S. Cl.
CPC .............. *C07C 51/25* (2013.01); *B01J 23/52* (2013.01); *B01J 23/66* (2013.01); *B01J 35/0013* (2013.01); *B01J 37/0211* (2013.01); *B01J 37/0213* (2013.01)

(58) Field of Classification Search
CPC ...... B01J 35/026; B01J 23/10; B01J 37/0211; B01J 35/0013; B01J 37/0213; B01J 23/52; C07C 51/25; C07C 59/01

USPC .......................................... 562/539; 502/304
See application file for complete search history.

(56) References Cited

U.S. PATENT DOCUMENTS

| | | | | |
|---|---|---|---|---|
| 6,972,337 | B1 * | 12/2005 | Onimus ................... | B01J 29/44 549/531 |
| 9,458,079 | B2 * | 10/2016 | Kim ....................... | C07C 51/25 |
| 9,546,124 | B2 * | 1/2017 | Lee .......................... | B01J 23/66 |

FOREIGN PATENT DOCUMENTS

| | | |
|---|---|---|
| JP | 2008-540126 A | 11/2008 |
| WO | 2008092115 A1 | 7/2008 |
| WO | 2010110447 A1 | 9/2010 |

OTHER PUBLICATIONS

Abad et al. A Collaborative Effect between Gold and a Support Induces the Selective Oxidation of Alcohols. Angew. Chem. Int. Ed. 2005, 44, 4066-4069.*
Alberto Abad et al., "Unique gold chemoselectivity for the aerobic oxidation of allylic alchohols," ChemComm, 2006, pp. 3178-3180.
Cristina Della Pina, et al., "A green approach to chemical building blocks. The case of 3-hydroxypropanoic acid", Green Chemistry., 2011, vol. 13, pp. 1624-1632, www.rsc.org/greenchem, The Royal Society of Chemistry 2011.
Cristina Della Pina, et al., "Oxidation of Allyl Alcohol in the Presence of a Gold Catalyst: A Route to 3-Hydroxypropionic Acid", ChemSusChem 2009, vol. 2, pp. 57-58.
Qi Fu et al., "Active Nonmetallic Au and Pt Species on Ceria-Based Water-Gas Shift Catalysts", Science vol. 301, 2003, pp. 935-938, www.sciencemag.org., Aug. 15, 2003.
Ermelinda Falleta, et al., "Enhanced performance of the catalytic conversion of allyl alcohol to 3-hydroxypropionic acid using bimetallic gold catalysts", Faraday Discussion, The Royal Society of Chemistry 2011, vol. 152, pp. 367-379.

* cited by examiner

*Primary Examiner* — Yih-Horng Shiao
(74) *Attorney, Agent, or Firm* — Dentons US LLP (57) ABSTRACT

Disclosed herein are a heterogeneous catalyst for the preparation of 3-hydroxypropionic acid (3-HPA) from allyl alcohol, and a method for the preparation of 3-HPA from allyl alcohol using the catalyst. In the presence of the heterogeneous catalyst containing gold on a carrier, a liquid-phase reaction is conducted to produce 3-HPA from allyl alcohol at high yield.

16 Claims, 5 Drawing Sheets

HETEROGENEOUS CATALYST FOR PRODUCTION OF 3-HYDROXYPROPIONIC ACID FROM ALLYL ALCOHOL, AND METHOD FOR PREPARATION OF 3-HYDROXYPROPIONIC ACID FROM ALLYL ALCOHOL USING THE SAME

CROSS REFERENCE TO RELATED APPLICATION

This application claims the benefit of Korean Patent Application No. 10-2014-0134826, filed Oct. 7, 2014, which is hereby incorporated by reference in its entirety into this application.

BACKGROUND OF THE INVENTION

1. Technical Field

The present invention relates to a heterogeneous catalyst for preparing 3-hydroxypropionic acid (hereinafter referred to as "3-HPA") from allyl alcohol, and a method of preparing 3-HPA from allyl alcohol using the same. More particularly, the present invention relates to a method of preparing 3-HPA from allyl alcohol at a high yield by performing a liquid phase reaction in the presence of a heterogeneous catalyst including gold supported on a carrier composed of cerium oxide ($CeO_2$) or a composite oxide containing cerium oxide.

2. Description of the Related Art

Acrylic acid is the simplest unsaturated carboxylic acid, consisting of a vinyl group connected directly to a carboxylic acid terminus, and is a main raw material of superabsorbent polymers (SAPs), which are synthetic polymer materials having a capacity for absorbing 500 to 1000 times their own weight in moisture. Although practical for use in sanitary items, SAPs find now applications in a variety of fields including raw materials in soil conditioners for horticulture, water stopping agents for civil engineering and construction applications, sheets for raising seedlings, freshness preservatives for food distribution, goods for fomentation, and the like, in addition to sanitary items such as disposable diapers for children. Therefore, SAPs, known to have superior water absorbency as compared to conventional water-absorbing polymers, have become increasingly more widely used in practical applications, and thus their market value has become higher. Further, acrylic acid, used as a raw material of SAPs, has an important market value, too. Additionally, acrylic acid is used as an essential raw material of various kinds of goods (3000 or more), such as acrylic fibers, paints, adhesives, coating agents and the like.

Currently, the production of acrylic acid generally uses the route from fossil fuel through propylene and acrolein to acrylic acid. Since the first oil shock, there has arisen concern about the depletion of petroleum resources. Accordingly, it has become important to secure raw materials and various chemical bases from natural resources other than petroleum resources in terms of not only provision against the depletion of such petroleum resources, but also stability of industry basis substances independent of the price change of petroleum resources.

Meanwhile, with the rise of pro-environmental issues, biomass conversion techniques have attracted keen attention thanks to their advantage of utilizing various bio-based raw materials. The development of biomass-based acrylic acid is increasingly required, inter alia. There are suggested various reaction routes to biomass-based acrylic acid, including the glycerol-allyl alcohol-3HPA-acrylic acid route.

Glycerol is produced as a by-product in the process of producing a biodiesel from vegetable oils. Production of acrylic acid from allyl alcohol derived from glycerol enjoys the advantage of utilizing environment-friendly biomass rather than fossil fuel, as a source. WO 2008/092115 A1 discloses a method of obtaining allyl alcohol at a high yield by the reaction of glycerol and formic acid, without a catalyst. Therefore, the production of acrylic acid from allyl alcohol allows for the effective utilization of glycerol, a by-product of biodiesel, thereby improving the use efficiency of biodiesel, with the expectation of effective production from glycerol.

To date, many research reports have been established on the production of allyl alcohol from glycerol or the production of acrylic acid from 3-HPA, but with insufficiency found on the production of 3-HPA from allyl alcohol. Establishment of a process of producing 3-HPA from allyl alcohol would, therefore, complete the reaction route from glycerol to acrylic acid. For this, demand is placed on the development of a novel catalytic process.

Accordingly, there is a need for research into a novel method for preparing 3-HPA from allyl alcohol at high yield under a special synthesis condition.

PRIOR ART DOCUMENTS

Patent Document (Patent document 1) WO 2008/092115 A1

Nonpatent Documents (Nonpatent document 1) Green Chem. 2011, 13, 1624-1632
(Nonpatent document 2) ChemSusChem, 2009, 2, 57-58
(Nonpatent document 3) Science 301, 2003, 935-938

SUMMARY OF THE INVENTION

The present invention has been devised to solve the above-mentioned problems, and the object of the present invention is to provide a method of preparing 3-HPA from allyl alcohol at a high yield by a liquid phase reaction in the presence of a heterogeneous catalyst including gold supported on a carrier composed of cerium oxide ($CeO_2$) or a composite oxide containing cerium oxide.

In order to accomplish the above object, an aspect of the present invention provides a heterogeneous catalyst for preparing 3-HPA from allyl alcohol, wherein the catalyst includes gold nanoparticles, 7 nm or less in size, supported on a carrier composed of cerium oxide ($CeO_2$) or a composite oxide containing cerium oxide.

Another aspect of the present invention provides a method of preparing 3-HPA from allyl alcohol, including:

a) introducing a heterogeneous catalyst including gold nanoparticles, 7 nm or less in size, supported on a carrier composed of cerium oxide ($CeO_2$) or a composite oxide containing cerium oxide, into a mixed solution of a basic solution and allyl alcohol;

b) reacting the mixed solution for 1 to 30 h in a reactor set to have a partial oxygen pressure of 1 to 50 bar based on absolute pressure, and a temperature of 30 to 100° C. to give a liquid-phase reaction products containing 3-HPA; and c) separating 3-HPA from the liquid-phase reaction products.

According to the present invention, the heterogeneous catalyst can be used to produce 3-HPA from allyl alcohol by a liquid-phase reaction at a high yield (20~80%), with the concomitant production of acrylic acid at a yield of 0~30%.

In this case, the allyl alcohol conversion was 70% or higher. When combined with the already known processes of the production of allyl alcohol from glycerol and the production of acrylic acid from 3-HPA, the method of producing 3-HPA from allyl alcohol by oxidative reaction using the heterogeneous catalyst in accordance with the present invention can complete the biomass-based reaction route of glycerol-allyl alcohol-3-HPA-acrylic acid. Therefore, the present invention allows the production of the target product acrylic acid on a commercial scale, far more greatly contributing to the productivity of acrylic acid compared to conventional methods.

Over the conventional production route of acrylic acid from fossil fuel through propylene and acrolein, the production of 3-HPA from allyl alcohol derived from glycerol has advantage in terms of utilizing environment-friendly biomass. Therefore, when 3-HPA is produced from allyl alcohol, glycerol, as a by-product of biodiesel, can be effectively used, thereby increasing the economical efficiency of biodiesel and effectively producing 3-HPA from glycerol.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Below, a detailed description will be given of a heterogeneous catalyst for preparing 3-HPA from allyl alcohol and a method of preparing 3-HPA from allyl alcohol using the same according to the present invention.

The present invention addresses a method of preparing 3-HPA from allyl alcohol at a high yield using special synthesis conditions. By this method, therefore, 3-HPA can be produced at a remarkably high yield, compared to conventional methods.

1. Heterogeneous Catalyst for Preparing 3-HPA from Allyl Alcohol

The term "heterogeneous catalyst" used herein refers to a catalyst, generally in solid phase, that is different in phase from a material reacting therewith, and is advantageously separated from the reaction mixture with ease.

In detail, the heterogeneous catalyst of the present invention can be prepared by synthesizing gold nanoparticles from a gold precursor (salt compound), and impregnating the synthesized gold nanoparticle on a carrier. In one embodiment of the present invention, the impregnation of gold nanoparticles on a carrier is achieved by a colloidal deposition method.

In this context, the heterogeneous catalyst for preparing 3-HPA from allyl alcohol according to the present invention is characterized by gold nanoparticles, 7 nm or less and preferably 4 nm or less in size, supported on a carrier composed of cerium oxide ($CeO_2$) or a composite oxide containing cerium oxide. Given gold nanoparticles having the size, the heterogeneous catalyst exhibits excellent reactivity and selectivity. Smaller sizes of the gold particles result in higher yield of acrylic acid and 3-hydroxypropionic acid (3-HPA). In particular, when the size of gold particles is 4 nm or less, the yield of 3-HPA reaches as high as 50%. Accordingly, higher preference is made for a size of 4 nm or less in gold nanoparticles.

Also, gold may be contained in an amount of 5% by weight or less, and preferably in an amount of 0.0001 to 5% by weight, based on the total dry weight of the carrier. This content range is advantageous in that the reactivity of the catalyst is maximized with the minimized amount of the precious metal gold.

Conventionally, the carrier is made of activated carbon, titanium oxide ($TiO_2$), aluminum oxide ($Al_2O_3$), silicon oxide ($SiO_2$), zinc oxide ($ZnO_2$), zirconium oxide ($ZrO_2$), manganese oxide ($MnO_2$), iron oxide ($Fe_2O_3$), vanadium oxide ($V_2O_5$), tin oxide ($SnO_2$), or tungsten oxide ($WO_3$). However, the carrier useful in the present invention is made of cerium oxide ($CeO_2$) or a composite oxide containing cerium oxide.

2. Method of Preparing 3-HPA from Allyl Alcohol

So long as it can be applied to the production of 3-HPA, any commercially available allyl alcohol may be used in the method of preparing 3-HPA of the present invention, without limitation. Preferable is allyl alcohol with a purity of 60 to 99.9%.

The method of preparing 3-HPA from allyl alcohol in accordance with the present invention comprises:

a) introducing a heterogeneous catalyst including gold nanoparticles, 7 nm or less in size, supported on a carrier composed of cerium oxide ($CeO_2$) or a composite oxide containing cerium oxide, into a mixed solution of a basic solution and allyl alcohol;

b) reacting the mixed solution for 1 to 30 h in a reactor set to have a partial oxygen pressure of 1 to 50 bar based on absolute pressure and a temperature of 30 to 100° C. to give a liquid-phase reaction products containing 3-HPA; and c) separating 3-HPA from the liquid-phase reaction products.

In detail, preparation of the heterogeneous catalyst of the present invention may be achieved by impregnating a carrier with gold nanoparticles that may be synthesized from a gold precursor (salt compound). In one embodiment of the present invention, a colloidal deposition method may be used to impregnate gold nanoparticles on a carrier.

According to the present invention, the heterogeneous catalyst for preparing 3-HPA from allyl alcohol according to the present invention comprises gold nanoparticles as a catalytically active ingredient, the gold nanoparticles having a size of 7 nm or less and preferably 4 nm or less in size, and being supported on a carrier composed of cerium oxide ($CeO_2$) or a composite oxide containing cerium oxide. When the gold nanoparticles have the size specified above, the heterogeneous catalyst exhibits excellent reactivity and selectivity. In addition, acrylic acid and 3-hydroxypropionic acid (3-HPA) can be obtained at higher yield as the gold particles become smaller in size. Particularly, when the size of gold particles is 4 nm or less, the yield of 3-HPA reaches as high as 50%. Accordingly, higher preference is made for gold nanoparticles with a size of 4 nm or less.

Further, the content of gold in the catalyst may be 5% by weight or less, and preferably 0.0001 to 5% by weight, based on the total dry weight of the carrier. This content range is advantageous in that the reactivity of the catalyst is maximized with the minimized amount of the precious metal gold.

Conventionally, examples of the material for the carrier include activated carbon, titanium oxide ($TiO_2$), aluminum oxide ($Al_2O_3$), silicon oxide ($SiO_2$), zinc oxide ($ZnO_2$), zirconium oxide ($ZrO_2$), manganese oxide ($MnO_2$), iron oxide ($Fe_2O_3$), vanadium oxide ($V_2O_5$), tin oxide ($SnO_2$), or tungsten oxide ($WO_3$). However, the carrier useful in the present invention is made of cerium oxide ($CeO_2$) or a composite oxide containing cerium oxide.

In step a), the basic solution is introduced so as to activate the oxidation reaction of allyl alcohol. The basic solution may be a solution of a basic compound comprising an alkali metal or an alkali earth metal in water. More specifically, the basic compound may include at least one selected from the group consisting of sodium hydroxide, lithium hydroxide, potassium hydroxide and calcium hydroxide.

The basic compound contained in the basic solution may be preferably used in an amount of 0.01 to 10 mol, and more preferably in an amount of 2 to 5 mol, per mole of allyl alcohol. The content of the basic compound has an influence on the conversion of allyl alcohol and the yield and selectivity of acrylic acid, 3-HPA and glyceric acid.

Further, the acid products, acrylic acid and 3-hydroxypropionic acid (3-HPA), may be obtained in the form of a salt by the addition of the basic compound.

For a batch-type process, the heterogeneous catalyst of step a) may be preferably used in an amount of 0.1 to 10.0 parts by weight, based on 100 parts by weight of the mixed solution of the basic solution and allyl alcohol. When used in an amount less than 0.1 part by weight, the heterogeneous catalyst is difficult to bring into sufficient contact with the reactants, resulting in a decrease in reaction rate. On the other hand, an amount of the catalyst exceeding 10.0 parts by weight is economically disadvantageous because the cost increases.

When the heterogeneous catalyst is used in a continuous process, its space velocity, which is calculated by the entering volumetric flow rate of the mixed solution of the basic solution and allyl alcohol per catalyst bed volume, preferably ranges from 0.1 to 20 $h^{-1}$. For example, given a space velocity less than 0.1 $h^{-1}$, the catalyst should be used in a large amount, incurring an increase in cost. On the other hand, at a space velocity exceeding 20 $h^{-1}$, the catalyst is in insufficient contact with the reactant, thus decreasing the reaction rate.

In step b), the reactor is set to have a partial oxygen pressure of 1 to 50 bar based on the absolute pressure. This partial oxygen pressure may be established by feeding an oxygen-containing gas to the reactor. For reaction, the temperature in the reactor is raised to 30 to 100° C. concurrently with or subsequently to the oxygen feeding. When the internal temperature of the reactor is below 30° C., the oxidative reaction rate becomes very slow, resulting in a great decrease in the conversion of allyl alcohol. On the other hand, at higher than 100° C., many side reactions occur, greatly decreasing the selectivity. Duration of the reaction is preferably set to range from 1 to 30 h. In one embodiment of the present invention where the $Au/CeO_2$ prepared by a colloidal deposition method is employed, 24 h is found to be an optimal reaction time.

The gas fed to the reactor may contain oxygen in an amount of 10% by volume or more, preferably in an amount of 20 to 100% by volume, and more preferably in an amount of 30 to 100% by volume. When the gas contains oxygen in an amount less than 10% by volume, the oxidation reaction progresses at a very low rate. In addition, the oxidative reaction is unlikely to occur at an oxygen partial pressure less than 1 bar. At an oxygen partial pressure exceeding 50 bar, the effect of pressure increase is insignificant.

Further, a reactor well known in the art, such as a batch reactor, a semi-batch reactor, a continuous stirred tank reactor (CSTR), a plug flow reactor (PFR), a fluidized bed reactor, etc. may be available in the step b).

The liquid phase reaction products may be at least one selected from the group consisting of acrylic acid, 3-HPA, and glyceric acid.

Separation of 3-HPA from the liquid phase reaction products in step c) may be achieved by means of acidification, ion exchange, extraction, crystallization, or distillation.

Since 3-HPA can be produced at a yield of 25% or greater, and preferably at a yield of 40% or greater, the preparing method of the present invention is economically very beneficial.

By the method of the present invention, the conversion of allyl alcohol is 70% or higher.

Hereinafter, the present invention will be described in more detail with reference to the following Examples. However, these Examples are set forth to illustrate the present invention, and the scope of the present invention is not limited thereto.

EXAMPLE 1

Preparation of Heterogeneous Catalyst for Preparing 3-HPA from Allyl Alcohol

A suspension of 2.9 mg of $HAuCl_4 \cdot 3H_2O$ and 66.3 mg of D-(+)-glucose in 100 mL of deionized water was added with 1.45 mg of $NaBH_4$ (0.38 mL DI water) while stirring to afford gold particles. A carrier (active carbon and metal oxide) was dispersed in 5 mL of DI water, and mixed with the gold particle suspension for 15 min while stirring. Following filtration, the filtrate was washed and dried to give a catalyst in which the gold particles were supported on the carrier.

EXAMPLE 2

Preparation of 3-HPA from Allyl Alcohol

A solution of 100 mg of the catalyst prepared by the method of Example 1 in a mixture of 17.24 mL of deionized water, 2.07 g of sodium hydroxide and 1.17 mL of allyl alcohol was put into a 50 mL glass reactor. After being degassed, the glass reactor was charged with gas having an oxygen partial pressure of 3 bar. Thereafter, the resulting solution was reacted at 50° C. for 24 h in the glass reactor. During the reaction, the oxygen partial pressure in the glass reactor was maintained at 3 bar. The liquid-phase reaction products thus obtained were qualitatively and quantitatively analyzed by high performance liquid chromatography (HPLC).

EXPERIMENTAL EXAMPLE

The liquid-phase reaction products prepared in Example 2 were analyzed for area % of acrylic acid, 3-hydroxypropionic acid and glyceric acid by high performance liquid chromatography (YL9100 HPLC, Young Lin Instrument Co.). Allyl alcohol conversion, selectivity for 3-HPA, and yield of 3-HPA were calculated using the following Math Equations 1 to 3, respectively.

$$\text{Allyl alcohol conversion (\%)} = 100 \times (\text{moles of allyl alcohol reacted})/(\text{moles of allyl alcohol fed}) \quad \text{[Math Equation 1]}$$

$$\text{3-HPA yield (\%)} = 100 \times (\text{moles of 3-HPA produced})/(\text{moles of allyl alcohol fed}) \quad \text{[Math Equation 2]}$$

Selectivity for 3-HPA can be calculated from data of both the allyl alcohol conversion and the 3-HPA yield using Math Equation 3.

Selectivity for 3-HPA (%)=100×(3-HPA yield)/(allyl alcohol conversion)  [Math Equation 3]

Figure 1:
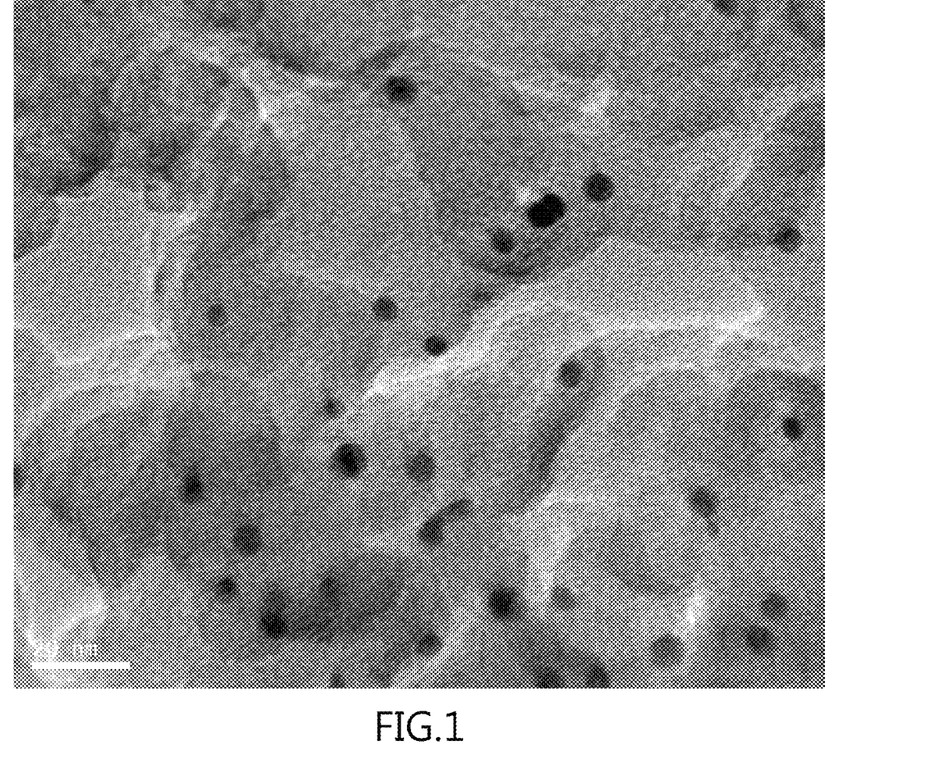
FIGS. 1 to 5 are TEM images of the heterogeneous catalysts prepared in the following Example, taken by transmission electron microscopy (JEM-2100, JEOL).
Figure 2:
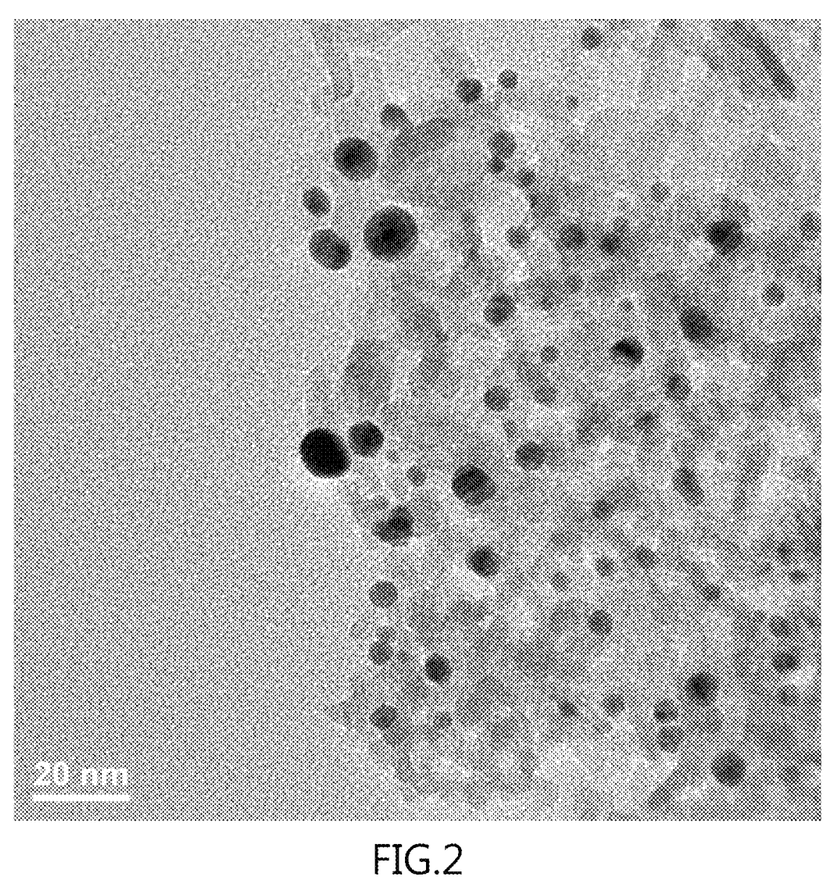
Figure 3:
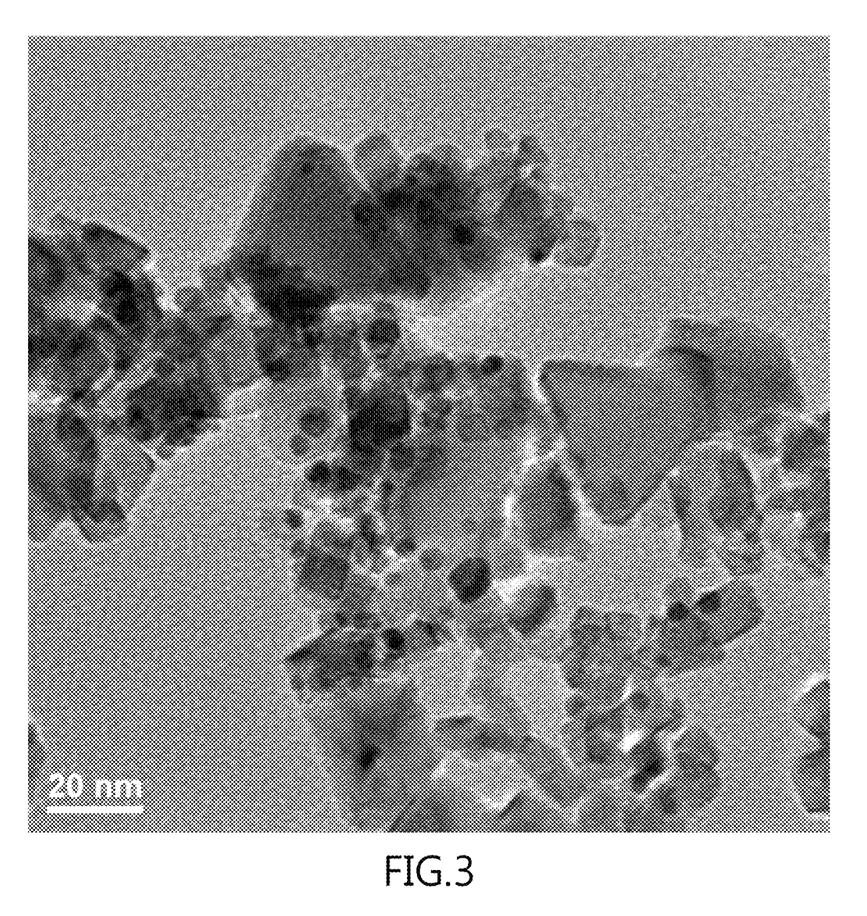
Figure 4:
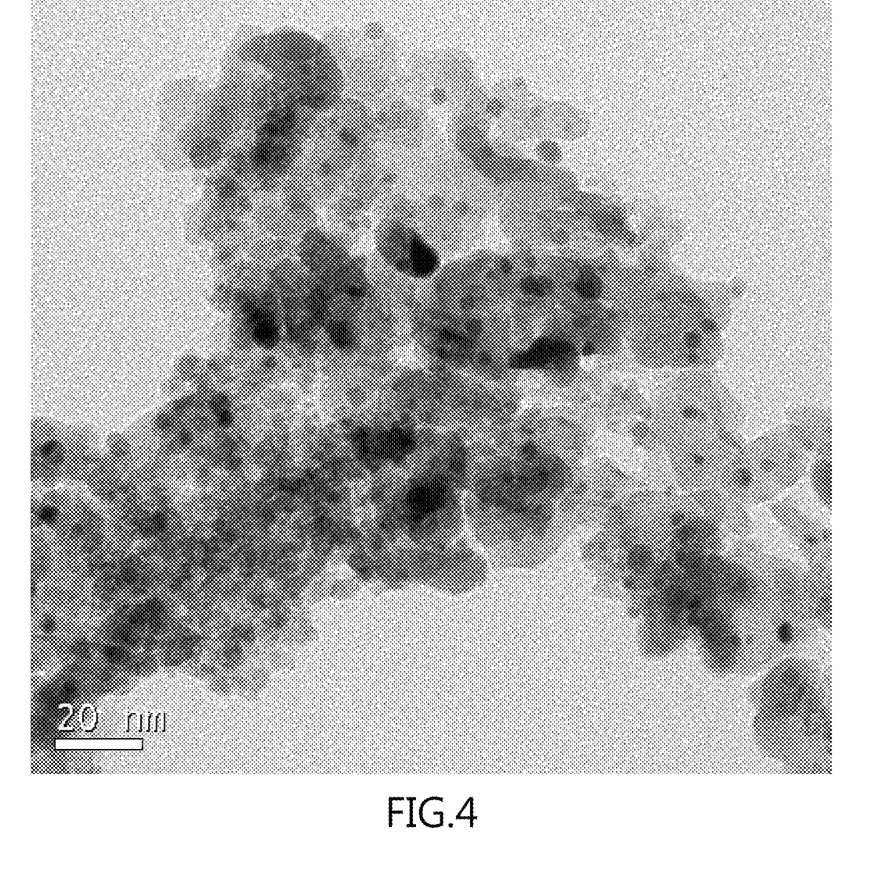
Figure 5:
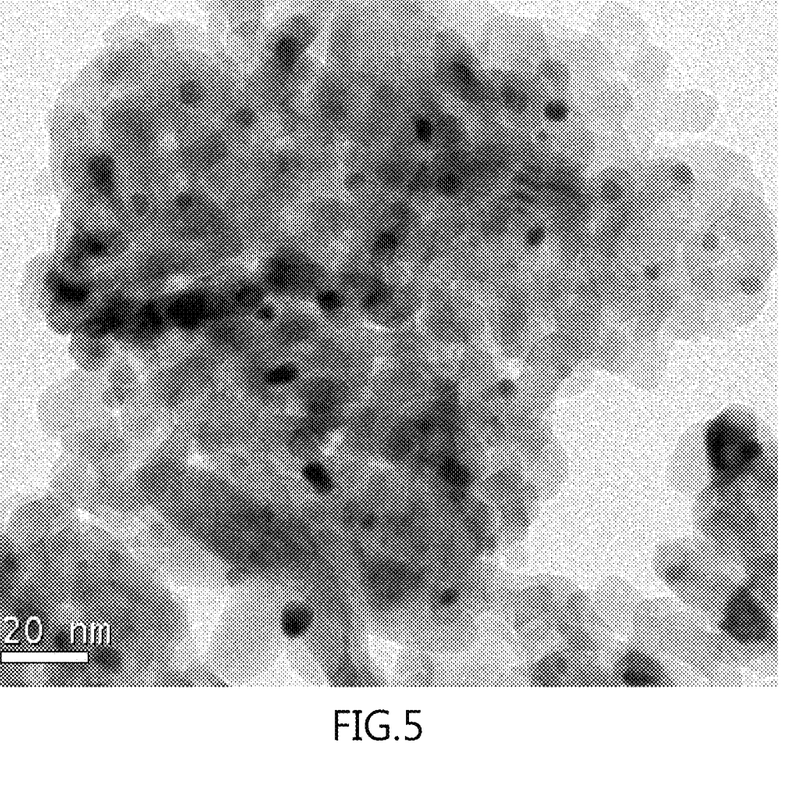

FIGS. 1 to 5 are TEM (JEM-2100, JEOL) images of the heterogeneous catalysts having gold particles of 4~5 nm size supported on the carriers activated carbon (FIG. 1), aluminum oxide ($Al_2O_3$) (FIG. 2), cerium oxide ($CeO_2$) (FIG. 3), iron oxide ($Fe_2O_3$) (FIG. 4), and titanium oxide ($TiO_2$) (FIG. 5), as prepared in Example 1.

Catalytic activities with gold nanoparticles supported on various carriers are summarized in Table 1, below. As is understood from the data, the activity was found to vary depending on the carrier. Here, the gold particle was set to have a size of 4.3 nm±1.00 nm.

TABLE 1

T = 50° C., allyl alcohol/metal = 4000, NaOH/allyl alcohol = 3, $pO_2$ = 3 bar, t = 24 h, solution 18.4 mL, catalyst ~100 mg, Au size = 4.3 nm ± 1.00 nm

| Catalyst | Conversion (%) | Yield (%) | | |
|---|---|---|---|---|
| | | 3-HPA | Acrylic acid | Glyceric acid |
| Au/C | 84.4 | 34.9 | 2.7 | 8.3 |
| Au/$Al_2O_3$ | 100 | 42.8 | 4.1 | 19.1 |
| Au/$CeO_2$ | 100 | 48.8 | 24.6 | — |
| Au/$Fe_2O_3$ | 99.2 | 41.0 | — | 16.3 |
| Au/$TiO_2$ | 99.8 | 28.2 | 9.6 | 16.7 |

In addition, considering that the size of gold nanoparticles would have influence on the selectivity of the products, the size of gold nanoparticles was set to be around 2.7 nm. Catalysts having gold particles with a size of around 2.7 nm were tested for activity with various carriers, and the results are summarized in Table 2, below. At the reduced size of gold particles, yields of the liquid-phase reaction products were generally increased. As can be seen in Tables 1 and 2, the highest yield of 3-HPA was obtained by the catalysts that employed cerium oxide ($CeO_2$) as a carrier on which gold particles different in size were supported. Moreover, cerium oxide ($CeO_2$) as a carrier was found to guarantee a higher yield of acrylic acid than do the other metal oxides.

TABLE 2

T = 50° C., allyl alcohol/metal = 4000, NaOH/allyl alcohol = 3, $pO_2$ = 3 bar, t = 24 h, solution 18.4 mL, catalyst ~100 mg, Au size = 2.7 nm ± 0.9 nm

| Catalyst | Conversion (%) | Yield (%) | | |
|---|---|---|---|---|
| | | 3-HPA | Acrylic acid | Glyceric acid |
| Au/C | 100 | 42.2 | 10.8 | 19.1 |
| Au/$Al_2O_3$ | 100 | 46.2 | 15.2 | 14.1 |
| Au/$CeO_2$ | 100 | 51.4 | 24.5 | — |
| Au/$TiO_2$ | 100 | 37.9 | 14.8 | 18.9 |

Then, the experiments were conducted to investigate the effect of NaOH concentration on the performance of the catalysts in the oxidative reaction of allyl alcohol, and the results are given in Table 3, below. As shown in Table 3, when activated carbon was used as a carrier, the yield of 3-HPA increased with an increase in the molar ratio of NaOH to allyl alcohol from 3 to 6, but both the conversion and the yield were decreased as the molar ratio of NaOH to allyl alcohol increased to 9. Thus, the catalyst having activated carbon as a catalyst was observed to be the most efficient at a molar ratio of NaOH/allyl alcohol of 6. The same experiment was performed on the catalyst having cerium oxide ($CeO_2$) as a carrier. For the catalyst Au/$CeO_2$, both the conversion and the yield were maximized when the molar ratio of NaOH/allyl alcohol was 3, as shown in the data of Table 3.

TABLE 3

T = 50° C. Tests were conducted using Au particles with a size of 2.7 nm at various NaOH concentrations under the condition of Table 1.

| Carrier | NaOH/AA | Conversion (%) | Yield (%) | | |
|---|---|---|---|---|---|
| | | | 3-HPA | Acrylic acid | Glyceric acid |
| $CeO_2$ | 0 | 100 | 40.4 | 17.9 | 11.6 |
| $CeO_2$ | 3 | 100 | 51.4 | 24.5 | — |
| $CeO_2$ | 6 | 80.0 | 43.9 | 14.6 | — |
| Carbon | 3 | 100 | 42.2 | 10.8 | 19.1 |
| Carbon | 6 | 100 | 54.5 | 11.2 | 4.7 |
| Carbon | 9 | 74.8 | 26.9 | 3.6 | — |

For comparison, activated carbon and metal oxides that were used as carriers were tested for catalytic activity in the oxidative reaction of allyl alcohol. The results are summarized in Table 4, below. As can be seen, activated carbon and the metal oxides showed catalytic activities although different in conversion and yield, and thus are anticipated to act as catalysts to some degree. However, these carriers themselves were significantly lower in catalytic activity than the catalyst of the present invention in which gold is supported on a carrier.

TABLE 4

T = 50° C., allyl alcohol/metal = 4000, NaOH/allyl alcohol = 3, $pO_2$ = 3 bar, t = 24 h, solution 18.4 mL, catalyst ~100 mg

| Catalyst | Conversion (%) | Yield (%) | | |
|---|---|---|---|---|
| | | 3-HPA | Acrylic acid | Glyceric acid |
| Carbon | 28.1 | 14.6 | — | 4.3 |
| $Al_2O_3$ | 65.5 | 19.5 | — | 15.9 |
| $CeO_2$ | 65.0 | 23.2 | — | 19.0 |
| $Fe_2O_3$ | 100 | 13.7 | — | — |
| $TiO_2$ | 100 | 13.5 | — | 2.0 |

Further, gold nanoparticles, gold precursors, and carriers themselves were observed to produce 3-HPA at remarkably low yield. Only a catalyst having gold on a carrier guaranteed excellent catalytic activity. From the data obtained above, it is found that factors that influence the yield of 3-HPA include carrier type, NaOH concentration, reaction time, and temperature.

In conclusion, the heterogeneous catalyst of the present invention can be used to produce 3-HPA from allyl alcohol by a liquid-phase reaction at a high yield (20~80%), with the concomitant production of acrylic acid at a yield of 0~30%. In this case, the allyl alcohol conversion was 70% or higher. When combined with the already known processes of the production of allyl alcohol from glycerol and the production of acrylic acid from 3-HPA, the method of producing 3-HPA from allyl alcohol by oxidative reaction using the heterogeneous catalyst in accordance with the present invention can complete the biomass-based reaction route of glycerol-allyl alcohol-3-HPA-acrylic acid. Therefore, the present invention allows the production of the target product acrylic acid on a commercial scale, far more greatly contributing to the productivity of acrylic acid compared to conventional methods.

What is claimed is:

1. A heterogeneous catalyst for preparing 3-hydroxypropionic acid (3-HPA) consisting of gold nanoparticles having a size of 4 nm or less, supported on a carrier composed of cerium oxide ($CeO_2$) or a composite oxide containing cerium oxide,
   wherein the gold nanoparticles are supported on the carrier via impregnation using a colloidal deposition method.

2. The heterogeneous catalyst of claim 1, wherein the gold nanoparticles are synthesized from a gold salt compound.

3. The heterogeneous catalyst of claim 1, wherein the gold nanoparticles are contained in an amount of 5% by weight or less, based on the total dry weight of the carrier.

4. A method for preparing 3-hydroxypropionic acid (3-HPA) from allyl alcohol, comprising:
   a) introducing a heterogeneous catalyst of claim 1 into a mixed solution of a basic solution and allyl alcohol;
   b) reacting the mixed solution for 1 to 30 h in a reactor set to have a partial oxygen pressure of 1 to 50 bar based on absolute pressure, and a temperature of 30 to 100° C. to give a liquid-phase reaction products containing 3-HPA; and
   c) separating 3-HPA from the liquid-phase reaction products.

5. The method of claim 4, wherein the heterogeneous catalyst of step a) is prepared by synthesizing gold nanoparticles from a gold salt compound, and impregnating the synthesized gold nanoparticle on the carrier.

6. The method of claim 4, wherein the heterogeneous catalyst of step a) is used in an amount of 0.1 to 10.0 parts by weight, based on 100 parts by weight of the mixed solution of the basic solution and allyl alcohol when a batch-type process is conducted.

7. The method of claim 4, wherein the heterogeneous catalyst of step a) has a space velocity of 0.1 to 20 $h^{-1}$ for a continuous process.

8. The method of claim 4, wherein the gold nanoparticles of step a) are contained in an amount of 5% by weight or less, based on the total dry weight of the carrier.

9. The method of claim 4, wherein the liquid-phase reaction products contain 3-H PA alone or in combination with at least one selected from the group consisting of acrylic acid and glyceric acid.

10. The method of claim 4, wherein the basic solution of step a) is a solution of a basic compound comprising an alkali metal or an alkaline earth metal in water.

11. The method of claim 10, wherein the basic compound is selected from the group consisting of sodium hydroxide, lithium hydroxide, potassium hydroxide, calcium hydroxide, and a combination thereof.

12. The method of claim 10, wherein the basic compound contained in the basic solution is used in an amount of 0.01 to 10 moles per mole of allyl alcohol.

13. The method of claim 4, wherein the 3-HPA is produced at a molar yield of 25% or higher.

14. The method of claim 5, wherein the 3-HPA is produced at a molar yield of 40% or higher.

15. The method of claim 4, wherein molar conversion of allyl alcohol is 70% or higher.

16. The method of claim 4, wherein the reactor is selected from the group consisting of a batch reactor, a semi-batch reactor, a continuous stirred tank reactor (CSTR), a plug flow reactor (PFR), a fluidized bed reactor, and a combination thereof.

* * * * *